United States Patent
Neubauer et al.

(10) Patent No.: US 7,742,801 B2
(45) Date of Patent: Jun. 22, 2010

(54) PLANNING METHOD AND SYSTEM FOR FREE-FORM IMPLANT MODIFICATION

(75) Inventors: Timo Neubauer, Poing (DE); Manuel Millahn, Munich (DE)

(73) Assignee: BrainLAB AG, Feldkirchen (DE)

( * ) Notice: Subject to any disclaimer, the term of this patent is extended or adjusted under 35 U.S.C. 154(b) by 335 days.

(21) Appl. No.: 11/782,768

(22) Filed: Jul. 25, 2007

(65) Prior Publication Data

US 2008/0255445 A1    Oct. 16, 2008

Related U.S. Application Data

(60) Provisional application No. 60/822,704, filed on Aug. 17, 2006.

(30) Foreign Application Priority Data

Aug. 8, 2006    (EP) .................. 06016532

(51) Int. Cl.
*A61B 5/05* (2006.01)
*G06G 7/48* (2006.01)
*A61B 6/00* (2006.01)

(52) U.S. Cl. .................. 600/411; 703/11; 600/427; 378/21

(58) Field of Classification Search .................. 600/407, 600/411, 416; 378/21; 703/11
See application file for complete search history.

(56) References Cited

U.S. PATENT DOCUMENTS

| | | | | |
|---|---|---|---|---|
| 5,086,401 A | * | 2/1992 | Glassman et al. | ............ 700/259 |
| 5,299,288 A | * | 3/1994 | Glassman et al. | ............ 700/245 |
| 5,408,409 A | * | 4/1995 | Glassman et al. | ............ 600/407 |
| 5,879,354 A | | 3/1999 | Haines et al. | |
| 7,063,713 B1 | | 6/2006 | Butsch et al. | |
| 2003/0233094 A1 | | 12/2003 | Squires et al. | |
| 2004/0243134 A1 | | 12/2004 | Walker et al. | |

FOREIGN PATENT DOCUMENTS

| | | |
|---|---|---|
| DE | 199 04 640 | 8/2000 |
| EP | 0 456 103 | 11/1991 |

* cited by examiner

*Primary Examiner*—Eric F Winakur
*Assistant Examiner*—Michael T Rozanski
(74) *Attorney, Agent, or Firm*—Renner, Otto, Boisselle & Sklar, LLP

(57) ABSTRACT

A method for planning a bone implant ascertains a condition of a bone to be treated, and identifies a dysfunctional part of the bone. A free-form area then can be ascertained and registered, wherein the free-form area lies below the dysfunctional part. A control data set then is produced that forms the basis for ablating the bone on the ascertained free-form area.

21 Claims, 4 Drawing Sheets

PLANNING METHOD AND SYSTEM FOR FREE-FORM IMPLANT MODIFICATION

RELATED APPLICATION DATA

This application claims priority of U.S. Provisional Application No. 60/822,704 filed on Aug. 17, 2006, which is incorporated herein by reference in its entirety.

FIELD OF THE INVENTION

The invention relates to bone implants and, more particularly, to a planning method and system for modifying a bone and/or a bone implant.

BACKGROUND OF THE INVENTION

In order to provide a joint replacement in the human body, it is necessary to prepare the bone and/or implant such that a proper fit is achieved. Further, the implant must fulfil the requirements of bio-functionality and, therefore, must be accurately arranged and orientated.

Prior to the availability of image-assisted or navigation-assisted surgery, the only way to orientate an implant was to predefine its modification by producing five planes with the aid of different positioning instruments such as, for example, an intramedullary pin. This technique is illustrated in FIG. 2, which shows a bone 1' that has been ablated on a sequence of five planes 3'. An implant 2' provided with a inner contour corresponding to the ablated bone 1' is shown placed onto the bone 1'.

The above method is very invasive, e.g., a great deal of bone material is ablated. Moreover, the orientation of the implant often is not very accurate.

Nowadays, navigated cutting blocks are used such that predefined areas on the bone can be ablated or produced. This improves the orientation of the implant, but smooth cuts still require significant bone removal.

SUMMARY OF THE INVENTION

A planning method and system is provided that enables a minimal amount of healthy or still usable bone material to be removed, while allowing a secured, well-modified and well-orientated implant to be placed. The planning method, which serves for modifying a bone and/or bone implant, includes the following:
  the condition of a bone to be treated can be ascertained by an imaging method, in particular by an x-ray method, a computer tomography method or a magnetic resonance tomography method;
  a dysfunctional part of the bone is determined, for example, by computer-assisted graphical segmentation;
  the area of the bone that lies just below the dysfunctional part or lies below the dysfunctional part by a predetermined distance is ascertained and registered as a free-form area; and wherein
  a control data set is produced that can form the basis for ablating the bone on the ascertained free-form area using a navigation-assisted ablating device.

A difference between the above method and the prior art is that the planning method assists in producing a free-form area, and such a free-form area can be much more flexibly configured than prescribed, flat and/or straight planes that are achieved using cutting blocks. This increased configuration flexibility can save a great deal of functional bone material and, thus, this bone material is available in revision operations.

The ascertained and registered free-form area can be variously and expediently formed. Thus, it is possible on the one hand to ascertain and register the area in such a way that a particular safety distance from the dysfunctional part is always maintained (e.g., from the boundary between the healthy bone tissue and the dysfunctional part of the bone). This saves the most bone. Further, the contact side of the implant could correspondingly be modified to the new free-form surface.

On the other hand, it is of course possible to ascertain and register an area which, while lying entirely below the dysfunctional part, is however primarily modified to an available implant. The available implant, for example, may be an implant that can already have been outsourced in various sizes, wherein for example a free-form area could be ascertained that leaves a predetermined residual radius on the bone, in order to prepare it for the nearest-fitting implant.

It is possible to form a counter area on the implant, corresponding to the free-form area on the bone. The method thus affords the advantage of automatically orientating the implant, since the free-form area already taken into account in the planning stage for the bone also can be automatically contoured as a counter piece in the implant. Such free-form areas enable an improved grip or hold between the implant and bone, a better load distribution due to the improved surface matching and/or modification, and as already mentioned, fewer complications in revision treatments. In addition, the free-form areas also can be modified to pre-contoured inner sides of implants.

A control data set can be produced for guiding an ablating device guided by a free hand, wherein the ablating device can be positionally detected and tracked by means of a medical tracking system. On the basis of the control data set, assisting information and instructions for guiding the ablating device, which can be output via an image output device or the like, can be produced by a medical navigation system assigned to the tracking system.

The control data set can be produced for guiding an ablating device that is mechanically mounted and can be guided by hand, wherein the ablating device is positionally detected and tracked by means of the medical tracking system. On the basis of the control data set, assisting information, instructions and/or mechanical guiding aids for guiding the ablating device can be produced by a medical navigation system assigned to the tracking system.

The control data set can be produced for guiding an ablating device that is mechanically mounted and automatically guided (e.g., by a motion control device or the like), wherein the ablating device is positionally detected and tracked by means of a medical tracking system. On the basis of the control data set, control instructions for guiding the ablating device can be produced by a medical navigation system assigned to the tracking system.

In the latter two examples provide above, it is possible to produce the control data set for mechanically mounting or guiding a surgical robot that bears the ablating device. The control data set also can be produced for an ablating device that comprises a cutting tool, a jet cutting tool, a drilling tool, a milling tool, a laser ablating tool or a combination of two or more of these tools.

A system for modifying a bone implant comprises:
  a data processing means that produces a control data set which controls the ablation of a bone on a free-form area that has been ascertained as an area that lies just below a dysfunctional part of the bone or lies below the dysfunctional part by a predetermined distance; and a navigation-assisted bone ablating device that can ablate the bone on the free-form area.

The advantages already cited above for the planning method also apply to the above system.

The system can include a medical tracking system for positionally detecting and tracking the ablating device, and a medical navigation system that is assigned to the tracking system and provides guiding assistance for the ablating device on the basis of the control data set. The ablating device can be an ablating device that is guided by free hand, a mechanically mounted ablating device that can be guided by hand, or a mechanically mounted ablating device that can be guided by other means (e.g., automatically guided). The ablating device can be borne by a surgical robot that mechanically mounts or guides the device, and can comprise a cutting tool, a drilling tool, a milling tool, a laser ablating tool, a jet cutting tool or a combination of two or more of these tools. These tools are cited here as examples; any tools that are suitable for ablating substance on a bone are suitable for use with the present invention. The system can comprise an implant machining device that can form a bone abutting portion of a bone implant as a counter piece that fits the free-form area.

Using the planning method and system described herein, the orientation of the implant does not have to be predefined by planes but can be realized by the guiding of the navigation system. In other words, it is possible to plan so as to use an "offset" with respect to the dysfunctional or destroyed surface of the bone, e.g., ablating the dysfunctional surface or bone region and generating a new surface below the region that comprises bearing or "usable" bone material. The inner side of the implant may be correspondingly modified.

The system and method can improve the planning and preparation of the bone for endoprosthetic implants. The prior art bone saw, which produces flat, planar portions, can be replaced by a different technology such as for example laser cutting, jet cutting, hybrid laser cutting or milling.

When the operation is finally performed on the basis of the plan or with the aid of the system, the surgeon can register (positionally assign and identify in the navigation system) all the bones relevant for the implanting process, e.g., in an entire knee replacement operation or in operations on the upper or lower leg. Various techniques can be used for this, including, for example, CT-free registration using a navigated pointer instrument, or CT/MR-based registration using CT/MR images. Other registration techniques also can be used. The planning system then generates a surface which lies just far enough below the actual surface such that the entire dysfunctional tissue is removed and the surface can be modified to the nearest-fitting selected implant. If bio-functionality is impaired, the surface can be shifted such that the orientation of the implant again provides correct bio-functionality. In order to produce the surface, the ablating tool can be placed on an active or passive robot arm, which, assisted by the planning, provides a guide for the tool or guides the tool itself.

BRIEF DESCRIPTION OF THE DRAWINGS

The forgoing and other features of the invention are hereinafter discussed with reference to the drawing.

DETAILED DESCRIPTION

Figure 1:
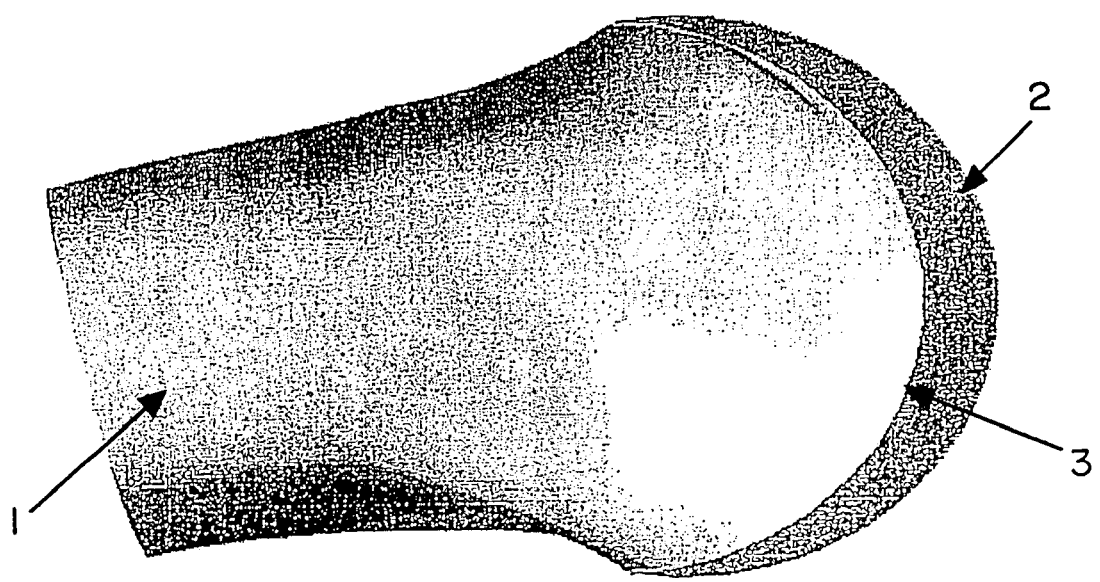
FIG. 1 illustrates a bone with an implant and an exemplary free-form modification in accordance with the invention.
Figure 2:
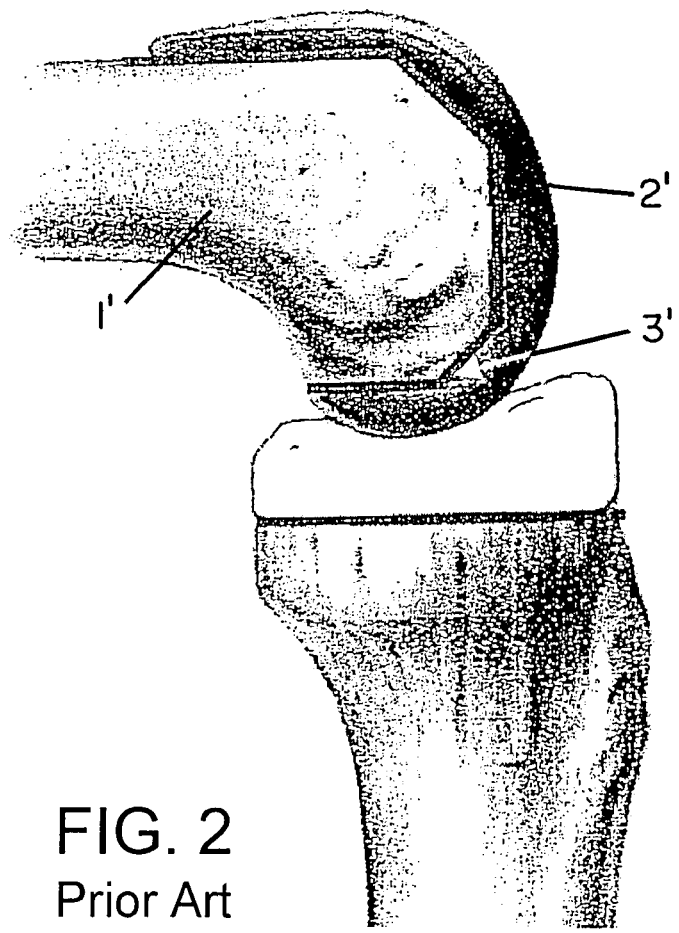
FIG. 2 illustrates an implant modification in accordance with the prior art.

FIG. 1 shows a bone 1 wherein an implant 2 has been modified and attached to the bone. The exemplary implant 2 is configured to be round on its outer side, and its inner side has a form which is accurately modified to a free-form area 3 formed on the bone 1 based on a method described herein. It can be seen that the surface 3 of the bone 1 in the region of the implant 2 no longer consists of a sequence of smooth or flat planes, as has been the case in accordance with the prior art (see, e.g., FIG. 2), but rather exhibits a free form that shows bearing, healthy and functional bone material at each point on the surface 3. When comparing FIGS. 1 and 2, it can be seen that significant bone material is saved using the free-form method described herein relative to the prior art.

Although the free-form area 3 is shown as a curved area, the shape may be any shape that is conducive to retaining as much bone material as possible while providing a satisfactory support and bonding surface.

Figure 3:
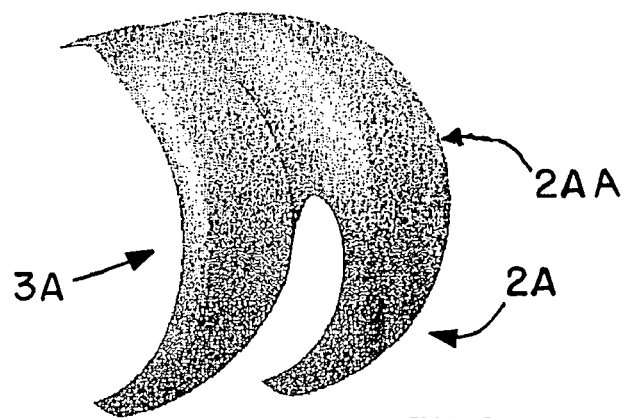
FIGS. 3 and 4 illustrate exemplary implant forms comprising free-form modifying areas in accordance with the invention.
Figure 4:
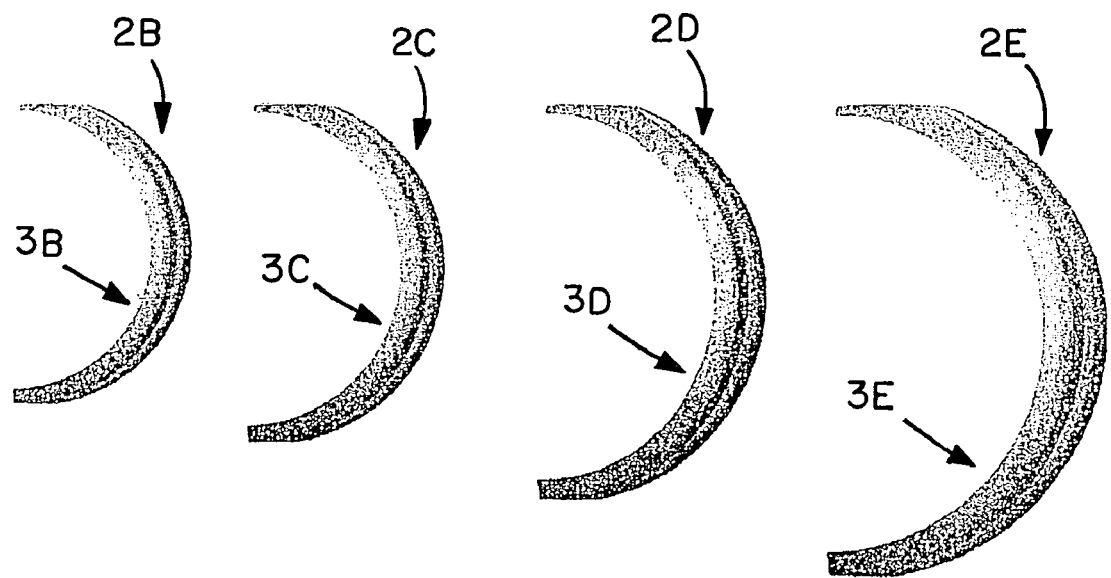

FIGS. 3 and 4 show a perspective view of implants in various embodiments. The implant 2A shown in FIG. 3 has a relatively complicated outer form 2AA, modified to the requirements of the exemplary application, and an inner form 3A that fits the produced free-form area of the bone (not shown in FIG. 3). It is noted that the free-form area of the bone can be modified to implants that, for example, are already available (e.g., generic or standard implants) or to so-called custom implants, wherein it can also be conceded that slightly more bone material is occasionally ablated. By using a free form method, a significant amount of bone material remains relative to methods in accordance with the prior art.

FIG. 4 shows a selection of exemplary implants 2B to 2E having various overall sizes and also different inner contours 3B to 3E. If, after image detection, the largest functional outer area of the bone is determined, one of the implants 2B to 2E can be selected, namely the one that best fits the "healthy surface of the bone" in terms of its outer contour and inner contour. The free-form area on the bone 1 then can be planned such that it fits the best-fitting implant 2B-2E. In particular cases, it is also possible to additionally modify the implant 2B-2E to the inner and/or outer area of the bone 1.

Figure 5:
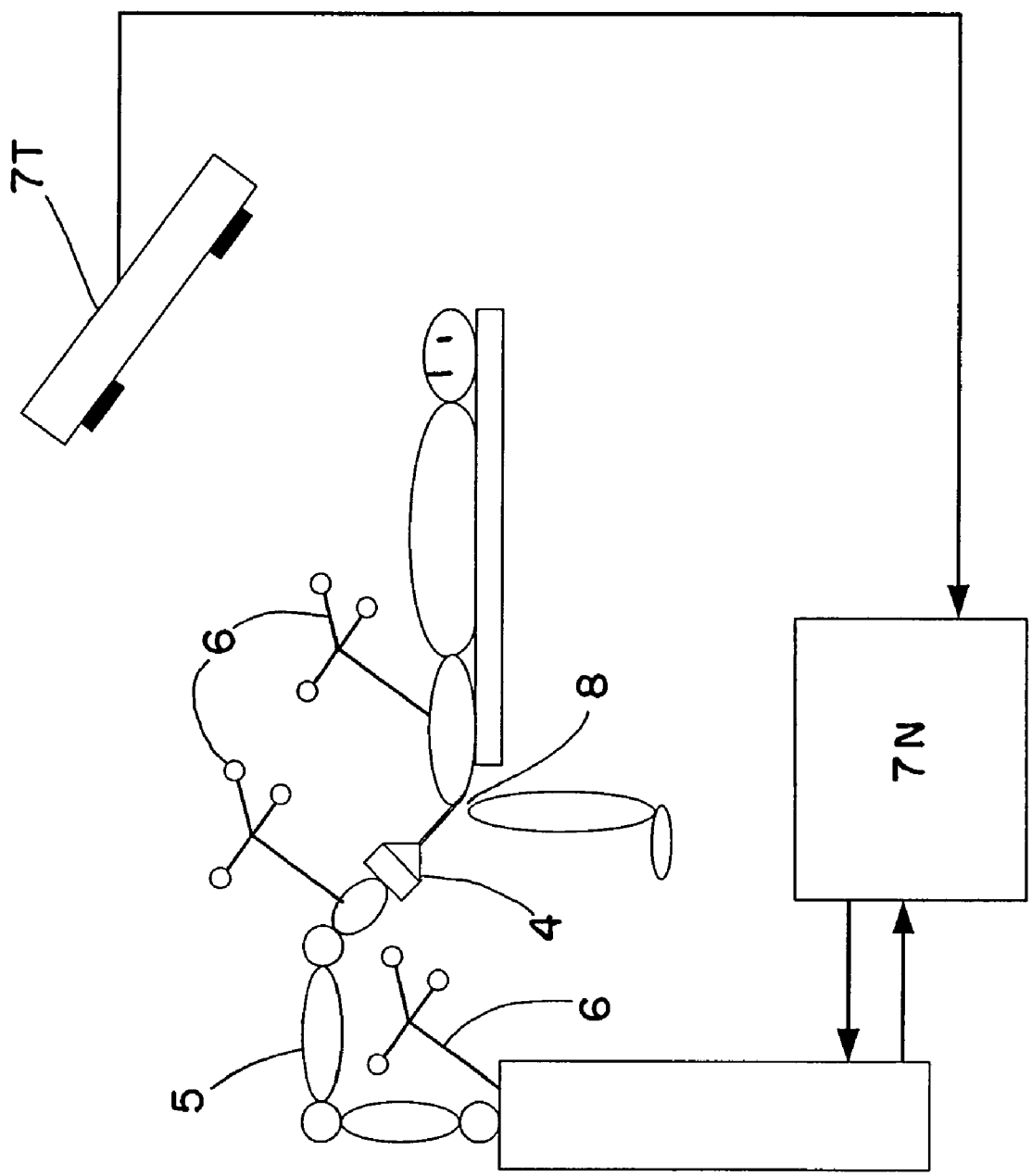
FIG. 5 illustrates an exemplary system for free-form implant modification in accordance with the invention.

An operation using planning assistance as described herein can be performed using an exemplary system as shown in FIG. 5. FIG. 5 shows a laser ablating tool 4 attached to the arm 5 of a surgical robot 6 (e.g., on both the robot's lower base body and on its final arm member). The robot 6 can be positionally localized and tracked by a camera tracking system 7T. The tracking system 7T can be assigned to a navigation system 7N, and the navigation system 7N can exchange data with the robot and receive data from the tracking system 7T. The robot, for example, can communicate data concerning the position of its joints or of the laser 4 to the navigation system 7N, wherein said positional information can be provided from joint sensors. Further, the navigation system 7N can transmit positioning instructions to the robot 6, e.g., the navigation system can communicate to the robot how the tool 4 is to be guided, where the tool 4 must not be guided, and/or when to halt movement of the tool 4. As a secondary or redundant position detection, the robot 6 also can be tracked by the tracking system 7T via the two reference arrays 6 arranged on its base and on its final arm member.

FIG. 5 also shows that the laser 4 is operating at the end of the upper leg bone of a patient, wherein the point currently being machined by the laser 4 is indicated by the reference sign 8. The upper leg or upper leg bone of the patient also can be positionally tracked by the navigation/tracking system and registered therein, such that the operational sequence in producing the free-form area runs exactly according to the planning in accordance with the method.

Such an operational sequence, which can be performed independently of the planning method and/or chronologically according to it, can be as follows: if an entire knee replacement operation or a partial replacement (of for example only one condyle) is envisaged, the first step may be to obtain access to the joint through the tissue, and the surface which is to be replaced then can be registered. The nearest-fitting implant then can be selected in accordance with the planned ablation depth, and the dysfunctional tissue is ablated as planned, for example by laser cutting, jet cutting or hybrid laser cutting. Since these techniques are capable of producing a free form, the form of the remaining bone can be well-modified, for example to the inner form of already available implants or of an implant separately produced for the patient.

Figure 6:
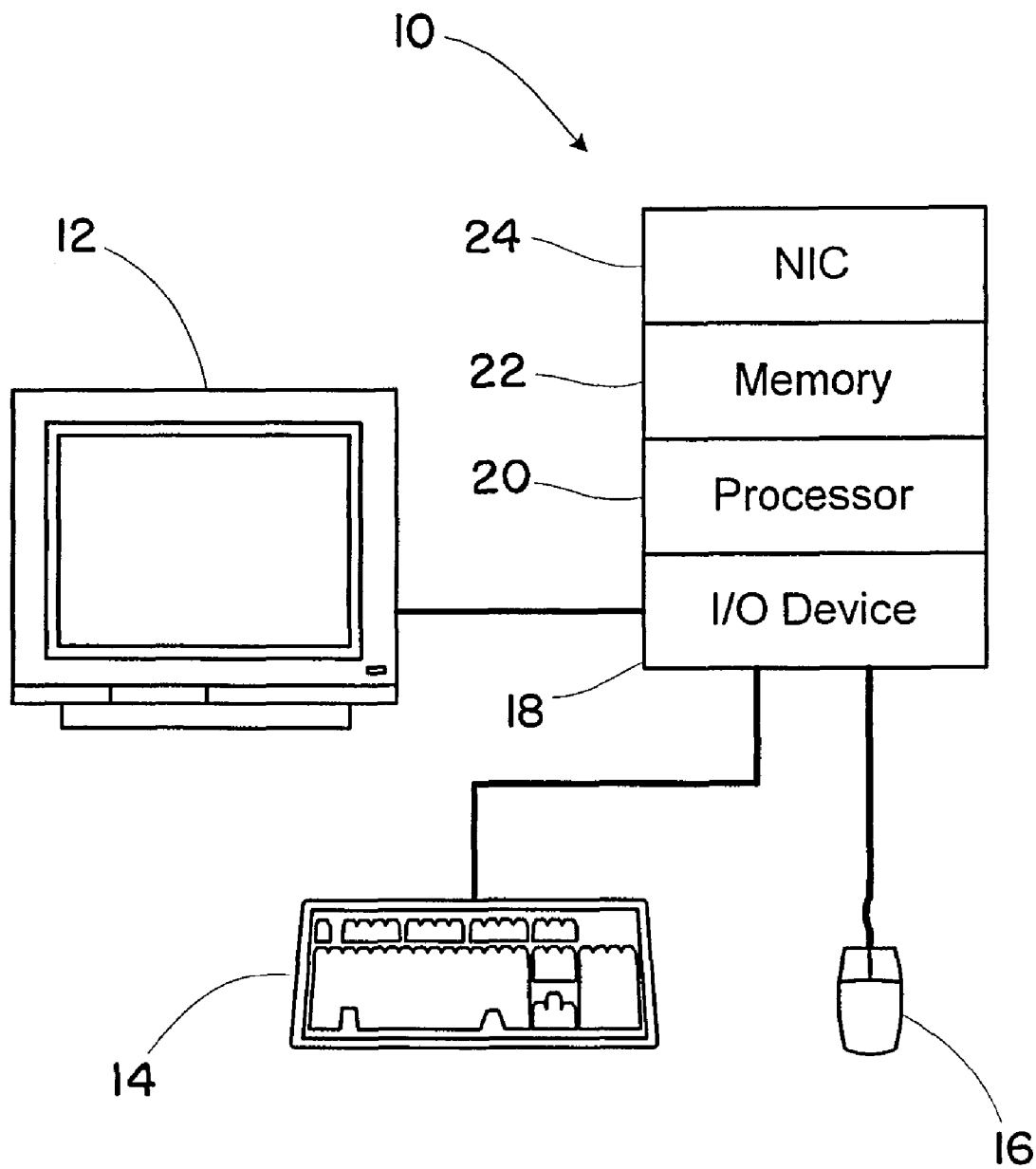
FIG. 6 is a block diagram of an exemplary computer system that can be used to carry out the method in accordance with invention.

Moving now to FIG. 6 there is shown a block diagram of an exemplary computer system 10 that may be used to implement one or more of the methods described herein. The computer system may be a stand alone system, or it may be part of the navigation system 7N described herein. The computer system 10 may include a display 12 for viewing system information, and a keyboard 14 and pointing device 16 for data entry, screen navigation, etc. A computer mouse or other device that points to or otherwise identifies a location, action, etc., e.g., by a point and click method or some other method, are examples of a pointing device 16. Alternatively, a touch screen (not shown) may be used in place of the keyboard 14 and pointing device 16. The display 12, keyboard 14 and mouse 16 communicate with a processor via an input/output device 18, such as a video card and/or serial port (e.g., a USB port or the like).

A processor 20, such as an AMD Athlon 64® processor or an Intel Pentium IV® processor, combined with a memory 22 execute programs to perform various functions, such as data entry, numerical calculations, screen display, system setup, etc. The memory 22 may comprise several devices, including volatile and non-volatile memory components. Accordingly, the memory 22 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 20 and the memory 22 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 24 allows the computer system 10 to communicate with other devices.

A person having ordinary skill in the art of computer programming and applications of programming for computer systems would be able in view of the description provided herein to program a computer system 10 to operate and to carry out the functions described herein. Accordingly, details as to the specific programming code have been omitted for the sake of brevity. Also, while software in the memory 22 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for planning a bone implant, comprising:

obtaining image data corresponding to a bone to be treated;

identifying in the image data a dysfunctional part of the bone and a functional part of the bone;

ascertaining a contour of an interface between the dysfunctional part of the bone and the functional part of the bone;

registering the ascertained contour in a medical navigation system, wherein registering the contour includes registering the contour a predetermined distance below the interface;

using a processor to produce a control data set based on the registered contour of the interface, said control data set forming the basis for ablating the bone; and outputting the control data set.

2. The method according to claim 1, wherein identifying the dysfunctional part and the functional part of the bone includes using an imaging method to ascertain the dysfunctional part and the functional part of the bone.

3. The method according to claim 2, wherein using the imaging method includes using an x-ray method, a computer tomography method or a magnetic resonance tomography method.

4. The method according to claim 2, wherein identifying includes using graphical segmentation of image data obtained from the imaging method to identify the dysfunctional part of the bone.

5. The method according to claim 1, further comprising using a navigation-assisted ablating device to remove the dysfunctional part of the bone based on the control data set.

6. The method according to claim 1, wherein producing the control data set includes producing a control data set that includes information for guiding an ablating device.

7. The method according to claim 6, further comprising:
positionally detecting and tracking the ablating device; and
based on the control data set and the detected and tracked position of the ablating device, providing information for guiding the ablating device via free hand.

8. The method according to claim 7, wherein positionally detecting and tracking the ablating device includes using a medical tracking system to detect and track the ablating device, and wherein the information for guiding the ablating device is provided by a medical navigation system communicatively coupled to said tracking system.

9. The method according to claim 6, further comprising:
positionally detecting and tracking the ablating device, wherein the ablating device is mechanically mounted to a support structure; and
based on the control data set and the detected and tracked position of the ablating device, providing information for guiding the ablating device by hand.

10. The method according to claim 9, wherein positionally detecting and tracking the ablating device includes using a medical tracking system to detect and track the ablating device, and wherein the information for guiding the ablating device is provided by a medical navigation system communicatively coupled to said tracking system.

11. The method according to claim 9, wherein providing information includes providing information to a surgical robot operatively coupled to the ablating device.

12. The method according to claim 1, wherein producing a control data set includes producing a control data set for guiding a mechanically mounted ablating device that is positionally detected and tracked, and, based on the control data set, producing control instructions for guiding the ablating device.

13. The method according to claim 12, wherein providing control instructions includes providing control instructions to a surgical robot operatively coupled to the ablating device.

14. The method according to claim 1, wherein producing the control data set includes producing a control data set for an ablating device comprising at least one of a cutting tool, a drilling tool, a milling tool, a laser ablating tool, a jet cutting tool.

15. A system for modifying a bone and/or bone implant, comprising:
a processor and memory;
logic stored in memory and executable by the processor, said logic comprising
logic that receives information corresponding to a contour of an interface between a dysfunctional part of the bone and a functional part of the bone;
logic that registers the contour in a medical workspace, wherein the logic that registers the contour includes logic that registers the contour a predetermined distance below the interface;
logic that produces instructions for directing the ablation of a bone based on the registered contour; and
a navigation-assisted bone ablating device operative to implement the instructions to ablate the bone.

16. The system according to claim 15, further comprising an implant machining device operative to form a bone abutting portion of a bone implant that fits the contour.

17. The system according to claim 15, further comprising:
a medical tracking system for positionally detecting and tracking the ablating device; and
a medical navigation system communicatively coupled to the tracking system, wherein the medical navigation system is operative to provide a guiding assistance for the ablating device based on the control data set and tracking data obtained from the tracking system.

18. The system according to claim 17, further comprising a surgical robot, wherein the ablating device is operatively coupled to the surgical robot.

19. The system according to claim 15, wherein the ablating device is an ablating device which is guided by a free hand, a mechanically mounted ablating device guided by hand, or a mechanically mounted ablating device that is automatically guided based.

20. The system according to claim 19, wherein the ablating device is operatively coupled to a surgical robot, and the surgical robot automatically guides the ablating device based on the instructions.

21. The system according to claim 15, wherein the ablating device comprises at least one of a cutting tool, a drilling tool, a milling tool, a laser ablating tool, or a jet cutting tool.

* * * * *